United States Patent [19]

Iwasaki et al.

[11] Patent Number: 4,976,825

[45] Date of Patent: Dec. 11, 1990

[54] PROCESS FOR RECOVERING N-METHYLPYRROLIDONE BY PLURAL DISTILLATIONS

[75] Inventors: Takao Iwasaki; Katsumi Horikoshi; Yuzo Yoshiji, all of Iwaki, Japan

[73] Assignee: Kureha Kagaku Kogyo Kabushiki Kaisha, Nihonbashi Horidome, Japan

[21] Appl. No.: 372,221

[22] Filed: Jun. 23, 1989

Related U.S. Application Data

[63] Continuation of Ser. No. 42,459, Apr. 24, 1987, abandoned.

[30] Foreign Application Priority Data

Apr. 28, 1986 [JP] Japan .................................. 61-98698

[51] Int. Cl.$^5$ .................. B01D 3/00; C07D 207/267; C08G 75/14
[52] U.S. Cl. .......................................... 203/71; 203/47; 203/73; 159/47.1; 159/901; 528/388; 528/501; 548/555
[58] Field of Search ........................ 203/88, 71, 73, 80; 159/2.1, 2.2, 2.3, 901, 47.1; 202/175; 548/555; 528/388, 501

[56] References Cited

U.S. PATENT DOCUMENTS

| | | | |
|---|---|---|---|
| 2,939,869 | 6/1960 | Carlson | 548/555 |
| 2,964,535 | 12/1960 | Clements . | |
| 3,687,907 | 8/1972 | Crouch et al. . | |
| 3,697,487 | 10/1972 | Cines . | |
| 3,783,138 | 1/1974 | Miles et al. . | |
| 3,919,177 | 11/1975 | Campbell . | |
| 3,941,664 | 3/1976 | Scoggin | 203/1 |
| 3,956,060 | 5/1976 | Scoggin | 159/47.1 |
| 4,501,902 | 2/1985 | Cleary | 548/555 |
| 4,645,826 | 2/1987 | Iizuka et al. | 528/388 |

FOREIGN PATENT DOCUMENTS

| | | |
|---|---|---|
| 45-3368 | 2/1970 | Japan . |
| 52-12240 | 4/1977 | Japan . |
| 61-7332 | 1/1986 | Japan . |
| 61-53324 | 3/1986 | Japan . |
| 61-53325 | 3/1986 | Japan . |
| 61-255933 | 11/1986 | Japan . |

OTHER PUBLICATIONS

Perry's Chemical Engineers' Handbook, Sixth Edition (1984) pp. (21-3)-(21-13).

Primary Examiner—Wilbur Bascomb
Attorney, Agent, or Firm—Janet I. Schwadron

[57] ABSTRACT

A process for recovering N-methylpyrrolidone contained in an N-methylpyrrolidone-containing liquid formed in the process for preparing a polyarylene thioether by the dehalogenosulfidation of a dihalogenoaromatic compound and an alkali metal sulfide in the presence of N-methylpyrrolidone as the polymerization solvent, which comprises (a) subjecting the N-methylpyrrolidone-containing liquid to distillation to distill and recover the majority of contained N-methylpyrrolidone while recovering a distillation residue having such a flowability that flow transferring of the distillation residue is possible, and (b) supplying the distillation residue to an air-tight mixer for a highly-viscous fluid, which has a vent and is provided with a heater, to treat the distillation residue under the conditions of a temperature in the mixer of 190° to 310° C., a pressure in the mixer of 50 to 760 Torr and a residence time in the mixer of 5 minutes to 10 hours, thereby to distill N-methylpyrrolidone contained in the distillation residue through said vent, the distilled N-methylpyrrolidone being collected. According to this process, N-methylpyrrolidone can be recovered at a high recovery without deterioration of the N-methylpyrrolidone.

2 Claims, 2 Drawing Sheets

PROCESS FOR RECOVERING N-METHYLPYRROLIDONE BY PLURAL DISTILLATIONS

This is a continuation of co-pending application Ser. No. 07/042,459 filed on Apr. 24, 1987 now abandoned.

BACKGROUND OF THE INVENTION

1. Field of the Invention

The present invention relates to a process for recovering N-methylpyrrolidone (hereinafter referred to as "NMP") in the preparation of a polyarylene thioether (hereinafter referred to as "PATE") by using NMP as the polymerization solvent.

More particularly, the present invention relates to a process for the recovery of NMP in which NMP left in the residue of a distillation column for the recovery of NMP in the post treatment process after termination of the polymerization reaction is recovered; the risk of ignition of the residue in the step of discharging the same from the distillation column is eliminated; generation of an unpleasant smell at the manufacturing site is prevented; and the NMP thus recovered is economically utilized again.

2. Prior Art

NMP is a typical heat-resistant organic polar solvent and has recently been valuably used as a polymerization solvent, especially for the production of PATE. However, since NMP is expensive, it is an indispensable condition for the industrial production of PATE from the economical viewpoint that NMP left in the reaction mixture liquid be recovered in a high yield after the polymerization reaction and that the recovered NMP be recycled to the polymerization process.

As a conventional method for recovering NMP contained in the reaction mixture liquid after the polymerization reaction process, a process in which a high-temperature reaction mixture liquid is subjected to adiabatic flashing to evaporate NMP and the NMP gas produced is cooled, condensed and recovered has been adopted (see, for example, U.S. Pat. No. 3,941,664 and U.S. Pat. No. 3,956,060 and Japanese Patent Application Laid-Open Specification No. 53324/86). According to this process, however, the recovery is low because the amount of NMP which is not evaporated but is left is considerably large, whereby the process is unsatisfactory from the industrial viewpoint.

As a measure for eliminating this disadvantage, a process in which NMP-containing liquids formed at various steps of the post-treatment process are finally collected irrespectively of whether or not adiabatic flashing is carried out, and the collected liquid is subjected to distillation by using a distillation column or the like for recovery of NMP has been proposed (see, for example, the specification of U.S. Pat. No. 3,783,138). However, since considerable amounts of solids such as oligomers and salts are contained in the collected NMP-containing liquid, the residue in the distillation apparatus (hereinafter referred to as "distillation residue") will lose flowability upon excessive distillation of NMP, and it will become difficult to discharge the distillation residue from the distillation apparatus.

Furthermore, if the distillation temperature is elevated to amply distill NMP, the contained organic substances such as NMP and PATE oligomers will become decomposed, and impurities having a higher boiling point than that of NMP will become mixed into NMP recovered and are apt to have adverse effects on circulation and re-use of NMP.

Accordingly, in the conventional process, the recovery by distillation of discharged NMP can be performed only to such an extent that the distillation residue will still be in the form of a sufficiently flowable slurry.

A large amount of NMP is thus still left in this slurry of the distillation residue, but according to the conventional technique, this NMP is burnt or discarded. This distillation residue slurry has a high vapor pressure of NMP because the temperature is high, whereby there have been environmental problems such as the risk of ignition, unpleasant smell of the slurry, and inhalation of gas by workers. Moreover, the loss of NMP in the recovery process results in increase of the manufacturing cost of PATE.

SUMMARY OF THE INVENTION

We carried out research with a view to recover thoroughly NMP from a distillation residue slurry still containing a considerable amount of NMP. As a result, it was found that, in order to expel a small amount of a low-boiling fraction from the distillation residue while preventing excessive heating of the distillation residue liquid, it is necessary that the space between the end of a stirring vane or stirring rotor and the wall surface in a heating wall portion be reduced, that the liquid be forcibly stirred to maintain a uniform temperature without local excessive heating in the highly viscous liquid, and that equipment having a guide mechanism for transportation of the viscous liquid and a small gas phase space portion for the distilled gas be provided. As the low-boiling fraction is expelled from the distillation residue liquid, the viscosity of the residue increases. It was found that if an air-tight mixer for a high-viscosity fluid, provided with a heater, is used as the NMP recovery apparatus, and the treatment is carried out under specific conditions so that excessive heating is not caused, a considerable amount of NMP can be industrially recovered from the above mentioned distillation residue. We have created the present invention on the basis of this finding.

More specifically, in accordance with the present invention, there is provided a process for recovering N-methylpyrrolidone contained in an N-methylpyrrolidone-containing liquid formed in the process for preparing a polyarylene thioether by the dehalogenosulfidation of a dihalogeno-aromatic compound and an alkali metal sulfide in the presence of N-methylpyrrolidone as the polymerization solvent, which comprises (a) subjecting the N-methylpyrrolidone-containing liquid to distillation to distill and recover the majority of N-methylpyrrolidone contained in the liquid while recovering a distillation residue having such a flowability that flow transferring of the distillation residue is possible, and (b) supplying the distillation residue to an air-tight mixer for a highly-viscous fluid, which has a vent and is provided with a heater to treat the distillation residue under the conditions of a temperature in the mixer of 190° to 310° C., a pressure in the mixer of 50 to 760 Torr, and a residence time in the mixer of 5 minutes to 10 hours, thereby to distill N-methylpyrrolidone contained in the distillation residue through said vent, the distilled N-methylpyrrolidone being collected.

The process for recovering NMP according to the present invention is characterized by, among others, the step (b), namely a step of recovering NMP from the distillation residue, and the process of the present invention can be regarded as one step of the post treatment of the polymerization process as a premise.

More specifically, according to the present invention, there is provided a process in which not only the economical effect of improving the recovery of the solvent in recovering and recycling the solvent used at the polymerization process but also the effect of preventing degradation of the quality of the product owing to accumulation of impurities by preventing decomposition of recovered NMP and recovering NMP with little deterioration and the effect of facilitating the disposal of the waste, eliminating the risk of ignition or combustion and preventing the worsening of the working environment by an unpleasant smell or the like can be attained. The final waste is solid at room temperature and hence, the final waste can be handled easily.

DETAILED DESCRIPTION OF THE PREFERRED EMBODIMENTS

NMP-Containing Liquid To Be Treated

Figure 1:
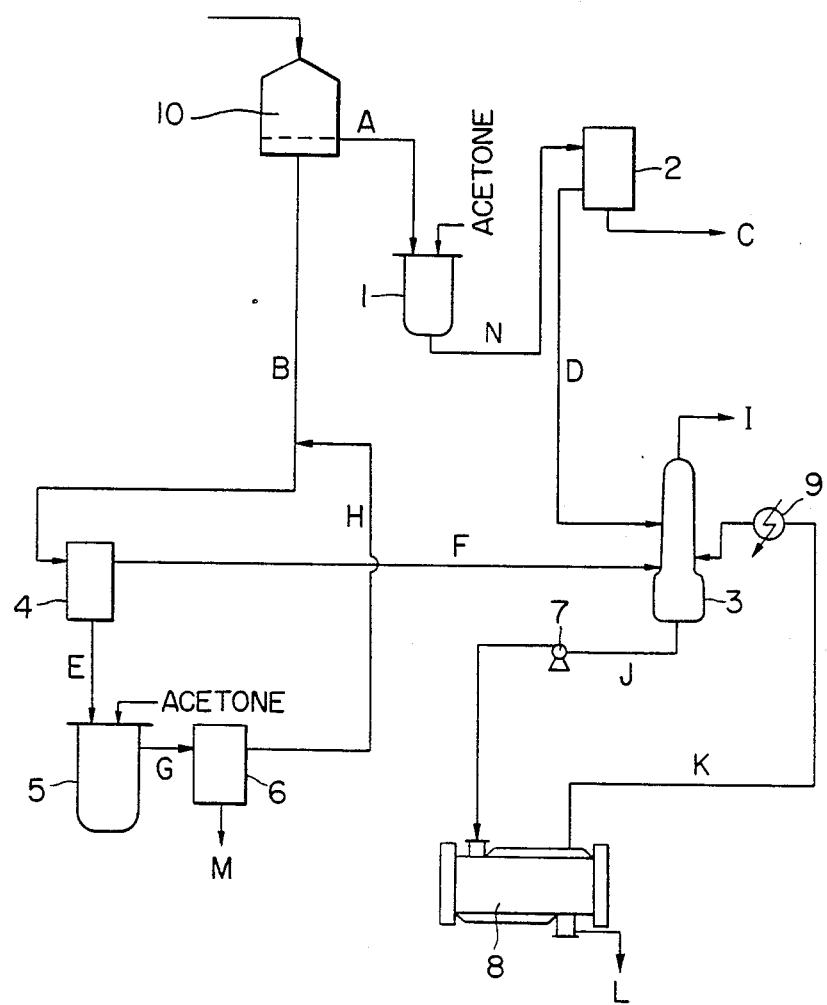
FIG. 1 is a flow chart illustrating the process for recovering N-methylpyrrolidone according to the present invention.

The NMP-containing liquid which is treated according to the process of the present invention is a liquid produced in the process for preparing PATE in which NMP or a mixed solvent composed mainly of NMP is used as the polymerization solvent.

A process in which PATE is formed by dehalogenosulfidation of a dihalogeno-aromatic compound with an alkali metal sulfide (an alkali metal halide is formed as a by-product) by using NMP or a mixed solvent composed mainly of NMP as the polymerization solvent is disclosed, for example, in Japanese Patent Publication No. 3368/70, Japanese Patent Publication No. 12240/77 and Japanese Patent Application Laid-Open Specification No. 7332/86.

In this reaction, adjustment of the water content in the reaction system is important, and water introduced into the reaction mixture as water of crystallization in the starting alkali metal sulfide or the like is distilled together with NMP. Moreover, after termination of the polymerization, such operations as separation, washing and drying are performed for recovering the intended PATE from the polymerization reaction mixture liquid. Various liquids containing NMP are generated in these steps.

As a process for the post treatment subsequent to the polymerization reaction, a process in which PATE alone is directly separated and recovered without diluting the reaction mixture with water can be mentioned (see Japanese Patent Application Laid-Open Specification No. 255933/86). In this process, used NMP which has been produced generally contains large amounts of solids such as salts and oligomers. Accordingly, this NMP-containing liquid is advantageously treated according to the process of the present invention.

Recovery of NMP according to Present Invention

The NMP-recovering process of the present invention comprises two steps, that is, the step (a) of subjecting the N-methylpyrrolidone-containing liquid obtained in the PATE-preparing process to distillation and collecting NMP recoverable by the distillation while leaving NMP not recoverable by the distillation as a distillation residue (which should be flowable so that transportation is possible), and the step (b) of treating the distillation residue obtained in the step (a) in an air-tight mixer provided with a heater to sufficiently distill NMP.

Since the step (a) is a conventional distillation step, it has no particular inventive feature.

The present invention is prominently characterized by the second step, that is, the step (b), of the two-stage treatment recovery process.

In the step (b), the objective NMP-containing slurry is heated in an air-tight mixer for a highly viscous fluid, which mixer has a vent and is provided with a heater, thereby to distill the NMP contained in the slurry. According to the present invention, the efficiency of recovery of NMP is improved by conducting the operation under specific conditions.

The air-tight mixer for a highly viscous fluid, which has a vent and is provided with a heater, used in the present invention, is basically an air-tight mixer for a highly viscous fluid and comprises a mixing chamber for containing a highly viscous fluid (NMP-containing slurry in the present invention) having a certain volume which is not excessively large as compared with the volume of the fluid and a stirrer or agitator for stirring the contained highly viscous fluid, wherein such an air-tightness is maintained that the pressure in the mixing chamber is maintained at a specific level (50 to 760 Torr in the present invention).

This mixer is constructed so that the highly viscous fluid contained in it is heated (at a temperature of up to about 310° C. in the present invention) by heating from the inner wall of the mixing chamber or from the outer wall of the stirrer, and a vent is formed in the mixing chamber so that the volatile component (NMP in the present invention) obtained during heating is distilled out through this vent. In the present invention, this mixer is utilized as a heating apparatus. Since in the present invention it is intended to recover NMP without deterioration thereof, it is preferable that the agitator be so constructed that the highly viscous fluid, that is, the NMP-containing slurry, is prevented from contacting the heating inner wall surface of the mixing chamber for a long period of time. That is, the agitator should be constructed so that the outer ends of the agitating vanes are not excessively spaced from the inner wall surface of the mixing chamber, and the material to be agitated can be moved in the mixing chamber.

The mixer of this type suitably used for carrying out the process of the present invention is preferably of the continuous type. In the mixer of the continuous type, the mixing chamber has an elongated shape like a cylinder or trough, and an inlet for the distillation column residue is formed on one end while a discharge outlet for the residue left after distillation of NMP is formed on the other end. The agitator has a structure such that the NMP-containing slurry is moved from the inlet to the discharge outlet. For example, a uniaxial or biaxial agitator comprising one rotor or a plurality of rotors, provided with screw-like, gear-like or plate-like blades, is used. A vent for distilled NMP is appropriately formed in the mixing chamber.

As the mixer of the above-mentioned type suitable for use in the present invention, for example, a twin-rotor mixer (inclusive of a self-wiping type) disclosed in paragraph 21-3, PERRY'S CHEMICAL ENGINEERS' HANDBOOK, 6th edition, can be used.

The conditions for recovering NMP from the distillation residue by using the above mentioned recovery apparatus will now be described.

The optimum temperature in the recovery apparatus depends on the pressure used in the apparatus, but it is generally preferable that the temperature be 190° to 310° C., especially 200° to 290° C. If the temperature is lower than 190° C., evaporation of NMP is insufficient, and good results cannot be obtained. The distillation residue becomes solidified, and transportation becomes difficult. On the other hand, if the temperature is higher than 310° C., NMP is thermally deteriorated in the apparatus, or impurities are accumulated and have an adverse influence on NMP.

The optimum pressure depends on the heating temperature used, but it is generally preferable that the pressure be 50 to 760 Torr, especially 100 to 500 Torr. A special air-tight structure and a pressure-reducing pump are necessary for reducing the pressure below 50 Torr, and the process becomes economically disadvantageous. The evaporation of NMP is insufficient under a pressure higher than 760 Torr, that is, in a compressed state, and good results cannot be obtained.

The optimum residence time of the distillation residue in the recovery apparatus depends on the NMP content in the distillation residue and the like, but it is generally preferable that the residence time be 5 minutes to 10 hours, especially 10 minutes to 3 hours. If the residence time is shorter than 5 minutes, the recovery of NMP is insufficient, and good results cannot be obtained. If the residence time exceeds 10 hours, there is a risk of thermal deterioration of NMP in the distillation residue.

In order to prevent deterioration of NMP, it is preferable that air or oxygen be removed from the interior of the apparatus by substitution with $N_2$ or other inert gas before initiation of the operation.

NMP discharged as the vapor from the apparatus is cooled and condensed and is recycled and used as the polymerization solvent directly or after re-distillation.

The concentrate mixture left after recovery of NMP contains almost no NMP, and therefore, after discharge from the apparatus, the concentrate mixture can be easily burnt or discarded.

The present invention will now be described more fully by way of the following examples that by no means are intended to limit the scope of the invention.

EXAMPLES 1 through 9

(1) Polymerization Process

A polymerization vessel equipped with an agitator and having a capacity of 2 m³ was charged with 700 kg of NMP and 370 kg of hydrous sodium sulfide (having a solid content of 45.85%), and the mixture was heated to about 202° C. to distill water and a small amount of NMP. Then, 315 kg of p-dichlorobenzene and 300 kg of NMP were added to the mixture, and polymerization was carried out at 20° C. for 4 hours. Then, 110 kg of water was additionally charged, and the temperature was elevated to 225° C., at which polymerization was carried out for 4.5 hours. After termination of the polymerization, the reaction mixture liquid was separated into a polymer A and a salt-containing NMP slurry B by using a polymer-separating apparatus 10.

(2) NMP Recovery Process

The recovery of NMP from the salt-containing NMP slurry was carried out according to the flow chart shown in FIG. 1.

Since a small amount of NMP was contained in the polymer A, acetone for extraction of NMP was added to the polymer A in an extraction tank 1. The obtained slurry containing NMP and acetone was separated into a wet polymer C and an NMP-containing acetone liquid D by a solid-liquid separator 2. The wet polymer C was washed with water and dried by a drier to recover dry PATE. On the other hand, the NMP-containing acetone liquid D separated in the solid-liquid separator 2 was supplied to a distillation apparatus 3.

The salt-containing NMP slurry B separated from the polymer A in the polymer-separating apparatus was separated into a solid E composed of salts and the like and an NMP-containing liquid F by a solid-liquid separator 4, and the NMP-containing liquid F was supplied to the distillation apparatus 3.

The solid E (composed mainly of salts) separated in the solid-liquid separator 4 still contained a considerable amount of NMP. In order to extract this NMP, acetone was added to the solid E in an extraction tank 5. The obtained NMP-containing acetone slurry G was subjected to solid-liquid separation in a solid-liquid separator 6, and since the liquid obtained was an acetone liquid H having a low NMP content, the acetone liquid H was joined with the salt-containing NMP slurry B coming from the polymer-separating apparatus before the solid-liquid separator to promote the solid-liquid separation in the solid-liquid separator 4.

Substantially all of NMP was thus collected in the distillation apparatus 3 in the form of a concentrated liquid containing a small amount of water or acetone, and the liquid was fractionated at the distillation apparatus 3 to recover NMP and acetone I. The distillation residue J left in the distillation apparatus 3 was a muddy slurry which could be transferred by a pump and comprised, for example, 17.1% by weight of oligomers, 21.5% by weight of salts, 60.5% by weight of NMP and other components.

For recovering NMP from this distillation residue slurry J, an air-tight horizontal twin-rotor continuous mixer 8 of the type heated by a heating medium from an outer wall jacket (inner volume of cylinder=8 liters, cylinder length=60 cm, provided with rotors having a plate-like blade, an openable and closable slurry introduction opening, an openable and closable discontinuous mixture withdrawal opening and an NMP discharge vent) was used, under the conditions that a rotating rate of the rotors were 20 RPM and the other conditions were varied, and the slurry J was fed batchwise to the NMP recovery apparatus 8 through a slurry pump 7. The contained NMP was evaporated to obtain a distillate K, and the distillate K was cooled and condensed by a condenser 9 and recovered. The concentrated residue L formed by this distillation was a tar-like liquid at high temperatures but was solid at room temperature. Every time the batchwise treatment was terminated, the concentrated residue L was discharged from the apparatus 8, and the NMP concentration in the recovered residue was determined. From this analysis value, the NMP recovery before and after the treatment were calculated. In this operation, the batchwise treatment was initiated after air in the apparatus 8 had been expelled by substitution with $N_2$.

The experiment was carried out 9 times. The obtained results are shown in Table 1. When the treatment temperature was high (300° C.) and the inner pressure was low (150 Torr), a recovery of 96% was obtained when the residence time was 60 minutes (Example 3).

TABLE 1

| Example No. | NMP Concentration (% by wt.) in Distillation Residue before Treatment | Heating Temperature (°C.) | Inner Pressure (Torr) | Residence Time (Minutes) | NMR Recovery (% by wt.) | Remarks |
| --- | --- | --- | --- | --- | --- | --- |
| 1 | 60.5 | 250 | 150 | 120 | 65 | |
| 2 | 60.5 | 275 | 150 | 60 | 94 | |
| 3 | 60.5 | 300 | 150 | 60 | 96 | |
|   | 60.5 | 80 | 150 | 360 | 5 | heating temperature was too low |
| 4 | 60.5 | 300 | 500 | 60 | 95 | |
| 5 | 60.5 | 300 | 760 | 60 | 85 | |
| 6 | 60.5 | 310 | 800 | 60 | 93 | |
| 7 | 60.5 | 300 | 150 | 3 | 8 | residence time was too short |
| 8 | 60.5 | 300 | 150 | 20 | 60 | |
| 9 | 60.5 | 300 | 150 | 120 | 93 | |

EXAMPLES 10 AND 11 AND COMPARATIVE EXAMPLES 1 AND 2

By using the distillation residue J described in Example 1, conditions for recovery of NMP in the same apparatus as used in Example 1 were analyzed to find out optimum ones (the residence time was set to 120 minutes). The results obtained are shown in Table 2.

At 180° C., the residue left after recovery of NMP was readily solidified and discharge of the residue was impossible. At 305° C., the presence of unknown components formed by decomposition of recovered NMP was observed.

Figure 2:
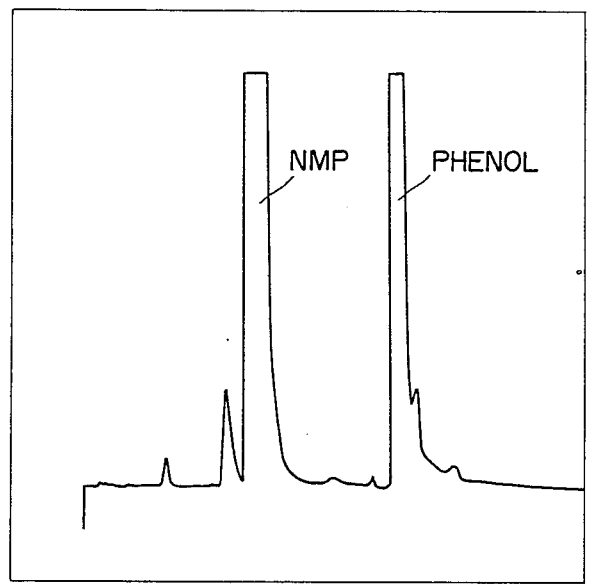
FIGS. 2 and 3 are gas chromatograms of N-methylpyrrolidone recovered in Example 10 and Comparative Example 1, respectively.
Figure 3:
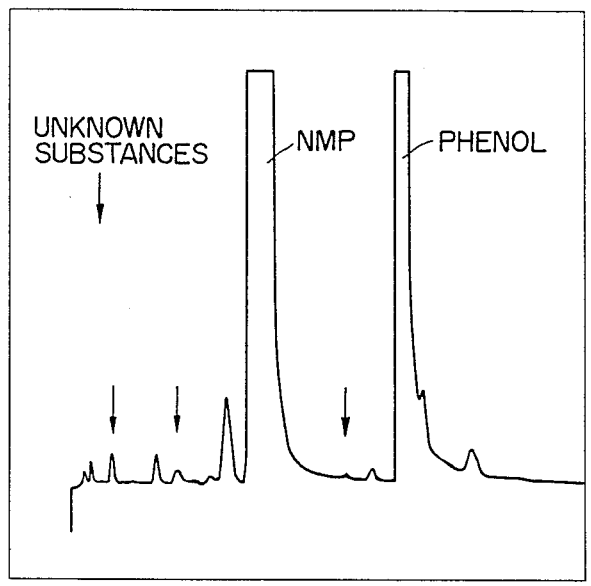

Gas chromatograms of NMP recovered in Example 10 and Comparative Example 1 are shown in FIGS. 2 and 3, respectively.

TABLE 2

|  | Exam. 10 (MAX) | Exam. 11 (MINI) | Comp. Exam. 1 | Comp. Exam. 2 |
| --- | --- | --- | --- | --- |
| Jacket temperature (°C.) | 300 | 220 | 310 | 200 |
| Inner temperature of apparatus (°C.) | 290 | 200 | 305 | 180 |
| Inner pressure (Torr) | 150 | 50 | 760 | 50 |
| Dischargeability | good | good | good | bad |
| Evaluation of recovered NMP | good | good | bad | good |

What is claimed is:

1. A process for recovering N-methylpyrrolidone-containing liquid formed in the process for preparing a polyarylene thioether by the dehalogenosulfidation of a dihalogenoaromatic compound and an alkali metal sulfide in the presence of N-methylpyrrolidone as a polymerization solvent, to form a reaction mixture which comprises (a) separating the reaction mixture after polymerization into polyarylene thioether and the N-methylpyrrolidone-containing liquid, (b) subjecting the N-methylpyrrolidone-containing liquid to distillation to distill and recover the majority of N-methylpyrrolidone contained in the liquid while recovering a distillation residue having such a flowability that flow transferring of the distillation residue is possible, and (c) supplying the distillation residue to a mixing apparatus wherein mixing of the residue is effected at a temperature of 190° to 310° C. and a pressure of 50 to 760 Torr with a residence time in the apparatus of 5 minutes to 10 hours in such a manner that the residue is ensured to maintain a uniform temperature without local excessive heating thereby to distill and recover N-methylpyrrolidone contained in the residue.

2. A process according to claim 1, wherein in each of the steps (b) and (c), the distillation residue is prevented from contacting an oxidative gas.

* * * * *